United States Patent
Hawkins et al.

(10) Patent No.: US 7,166,112 B2
(45) Date of Patent: Jan. 23, 2007

(54) DEVICE FOR DETERMINING DISTANCE BETWEEN TWO POINTS IN A SURGICAL SITE

(75) Inventors: J. Riley Hawkins, Cumberland, RI (US); Conor Russell McCrea, Brookline, MA (US); Christopher Lawrence Ramsay, New Bedford, MA (US)

(73) Assignee: Depuy Spine, Inc., Raynham, MA (US)

( * ) Notice: Subject to any disclaimer, the term of this patent is extended or adjusted under 35 U.S.C. 154(b) by 364 days.

(21) Appl. No.: 10/108,163

(22) Filed: Mar. 25, 2002

(65) Prior Publication Data

US 2003/0181920 A1 Sep. 25, 2003

(51) Int. Cl.
*A61B 17/64* (2006.01)

(52) U.S. Cl. ...................................................... 606/102
(58) Field of Classification Search ................ 606/102, 606/104, 80, 86, 87, 96, 97, 98, 99; 33/755, 33/512, 806

See application file for complete search history.

(56) References Cited

U.S. PATENT DOCUMENTS

| | | | | | |
|---|---|---|---|---|---|
| 3,738,355 | A | * | 6/1973 | Salvatore | 606/102 |
| 4,204,548 | A | * | 5/1980 | Kurz | 600/591 |
| 4,226,025 | A | | 10/1980 | Wheeler | |
| 4,263,903 | A | * | 4/1981 | Griggs | 606/75 |
| 4,450,834 | A | * | 5/1984 | Fischer | 606/80 |
| 4,726,121 | A | * | 2/1988 | Ray et al. | 33/806 |
| 4,885,862 | A | * | 12/1989 | Thayer | 43/6 |
| 5,013,318 | A | | 5/1991 | Spranza | |
| 5,071,420 | A | * | 12/1991 | Paulos et al. | 606/99 |
| 5,395,374 | A | * | 3/1995 | Miller et al. | 606/74 |
| 5,601,566 | A | * | 2/1997 | Dance et al. | 606/88 |
| 5,720,751 | A | * | 2/1998 | Jackson | 606/86 |
| 5,788,697 | A | * | 8/1998 | Kilpela et al. | 606/74 |
| 5,895,389 | A | * | 4/1999 | Schenk et al. | 606/96 |
| 5,989,259 | A | * | 11/1999 | Penenberg et al. | 606/99 |

* cited by examiner

*Primary Examiner*—Pedro Philogene

(57) ABSTRACT

A device for use by a surgeon to determine the distance between two points within a surgical site, the device having a gripper retractably and flexibly connected to a body by a retractor having a proximal spring portion and a distal portion comprising a cable.

4 Claims, 1 Drawing Sheet

DEVICE FOR DETERMINING DISTANCE BETWEEN TWO POINTS IN A SURGICAL SITE

FIELD OF THE INVENTION

This invention relates generally to spinal devices and more particularly to a device for measuring the distance between two spinal rods for selecting the appropriate size cross-connector to be implanted.

BACKGROUND OF THE INVENTION

A number of devices are available for measuring the distance between two points. Some of these have been adapted to work within a surgical wound. One of the most common measuring devices is a ruler. However, there are several problems with using a ruler to measure within a surgical wound. First, several size rulers are needed so that one is available that will fit within the wound. Often, the surgeon still has to cut the ruler to fit within the wound to obtain a measurement. Reading the measurement in the wound is often difficult because tissue, blood, and other fluids obscure the markings on the ruler. A ruler is difficult to use when measuring between two circumferential objects like spinal rods.

A three-sided ruler was designed to work better within the surgical site. Each side of the ruler measures a different distance, so that the ruler can be turned to obtain the most accurate distance. The reading must be done in the wound and the lighting is critical to make an accurate measurement. The same problems still exist with this modified ruler. Several sizes are needed to fit within the wound and measure the distance between sites. Accurate measurements are still difficult to read because the measurement is done in the wound with blood, tissue and other fluids in the way.

Another device used to measure between two points in surgery is the forceps or compass-type device. The device is inserted into the wound, one leg is directed at the first measuring point and the second leg is moved to the second point. The device is then removed from the wound and the distance between the two legs is measured against a ruler. This device requires an additional step and the measurement is less accurate because it is transferred to a ruler outside the wound. This device is also more expensive than the ruler.

U.S. Pat. No. 4,226,025 to Wheeler relates to a caliper for measuring the length, width, area and/or volume of living parts of mammals during surgery. The caliper includes a pair of long straight arms which are approximately parallel in a closed position and which pivot apart in a scissors movement in order to position the body part between the distal ends of each arm used for measuring. This device is useful for measuring cross-sectional areas or length of a line; however, it still is difficult to measure between two points such as spinal rods using this device because it has to be held in position against the object being measured and then compared to a measuring scale remote from the surgical site.

As noted above, prior art devices for measuring within a surgical site have either been not efficient or not very accurate. During a procedure the surgeon typically needs to measure the distance between two points to determine the appropriate size implant needed. An example use for this device is to aid the surgeon in determining the correct size cross-connector needed for additional stabilization of the spinal rods used for stabilizing adjacent vertebrae of the spine. There may be hooks or screws already placed on the rods which make placement of the cross-connector difficult. An accurate measurement of the distance between the two points on the rods to determine the size cross-connector is important to the surgeon and the patient as it can reduce the time of the surgery.

U.S. Pat. No. 3,738,355 ("Salvatore") discloses a bone gage for measuring the diameter of a bone. The device comprises a tube having an opening from which extends a longitudinal hook means 28. The jaws 29A,B of the hook means 28 open when covering sheath 40 is moved proximally. Longitudinal hook means 28 can not be retracted into the body, and so does not have axial translation capability relative to the opening.

U.S. Pat. No. 4,450,834 ("Fischer") also discloses a measuring device for measuring the diameter of a bone. The device comprises a tube having an opening from which extends a shouldered probe 174,182 extends. The probe is capable of axial translation within tubular body via axial translation of indicator tab 184. The shouldered probe is not retracted by a spring, and does not have radial translation capability relative to the first opening.

U.S. Pat. No. 5,013,318 ("Spranza") also discloses a measuring device for measuring the diameter of a bone. The device comprises a tube having a first opening from which whiskers 1 extend. The whiskers open by activation of knob 6. The whiskers can not be retracted back into the body, and so do not have axial translation capability relative to the first opening.

In sum, each of the bone gages discussed above are capable of providing essentially only line-of-sight measurement, and none provide a gripping means which can be both axially and radially translated from the opening of the body having the measuring scale.

X-rays, CT-imaging, and fluoroscope can also be used to measure distances between sites within the body. These methods require more time because the pictures need to be obtained and then measured either during or prior to the surgery. The equipment is also cumbersome.

It would therefore be desirable to provide an enhanced device for measuring the distance between two points within a surgical site having none of the disadvantages described above.

SUMMARY OF THE INVENTION

The present inventor has found that providing a gripping means which can be both axially and radially translated from the main body (and preferably flexibly retracted) solves the problems faced by the prior art. Because the gripping means may be moved in both radial and axial directions, this device provides more than line-of-sight measurement capability common to the conventional bone gages.

Therefore, in accordance with the present invention, there is provided a device for measuring two points comprising:
a) a hollow tubular body having a proximal portion and a distal portion, and a longitudinal bore defining a first opening in the distal portion,
b) retraction means having a proximal portion and a distal portion, the proximal portion being fixed to the proximal end portion of the hollow tubular body, and the distal portion extending through the first opening of the hollow tubular body, and
c) gripping means having a proximal portion and a distal portion, the proximal portion of the gripping means being attached to the distal end portion of the retraction means.

Also in accordance with the present invention, there is provided a device for use by a surgeon to determine the distance between two points within a surgical site, the device comprising:

a) a body having a measuring means associated therewith, b) retraction means, and c) gripping means, wherein the gripping means is fixedly connected to the body by the retraction means.

Also in accordance with the present invention, there is provided a device for use by a surgeon to determine the distance between two points within a surgical site, the device comprising:

a) a body having a measuring means associated therewith, and b) gripping means retractably and flexibly connected to the body.

Also in accordance with the present invention, there is provided a method of determining distance between two sites in a surgical wound, comprising;

a) providing a measuring device comprising a device for measuring two points comprising:

i) a hollow tubular body having a proximal portion and a distal portion, and a longitudinal bore defining a first opening in the distal portion, ii) retraction means having a proximal portion and a distal portion, the proximal portion being fixed to the proximal end portion of the hollow tubular body, and the distal portion extending through the first opening of the hollow tubular body, and iii) gripping means having a proximal portion and a distal portion, the proximal portion of the gripping means being attached to the distal end portion of the retraction means, b) locating the device at a first site within the surgical wound, c) moving either the first opening or the gripping means to a second site within the surgical wound while maintaining either the first opening or the gripping means at the first site, and d) viewing the measuring scale.

BRIEF DESCRIPTION OF THE DRAWINGS

These and other features of the invention will be understood from the description below, taken together with Figures which show illustrative embodiments and several variations and details of construction thereof, wherein.

DETAILED DESCRIPTION OF THE INVENTION

The present invention provides a device for determining the distance between two points in a surgical site.

Figure 1:
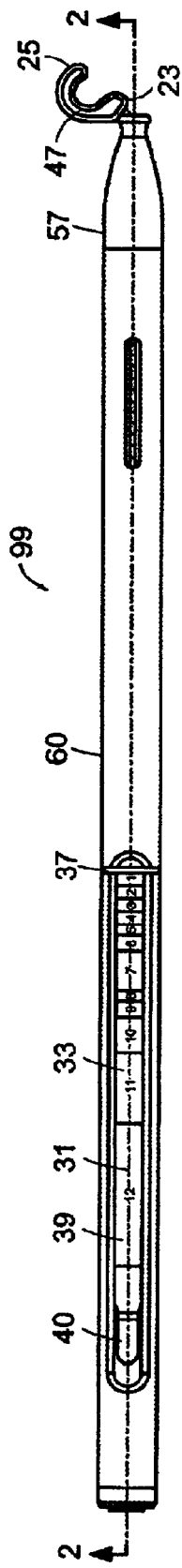
FIG. 1 shows a side view of the device of the present invention.
Figure 2:
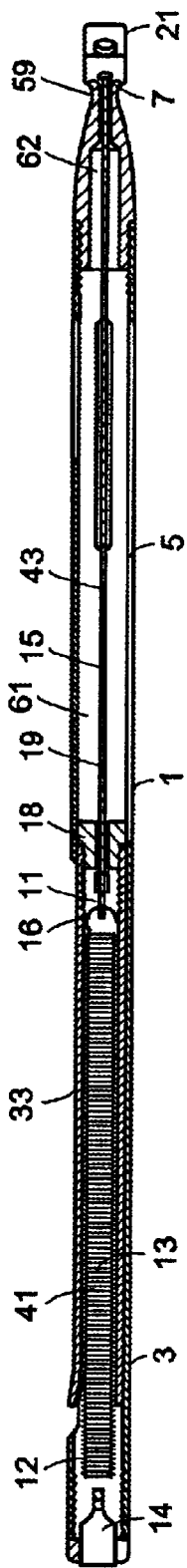
FIG. 2 discloses a longitudinal cross-section of FIG. 1.
Figure 3:
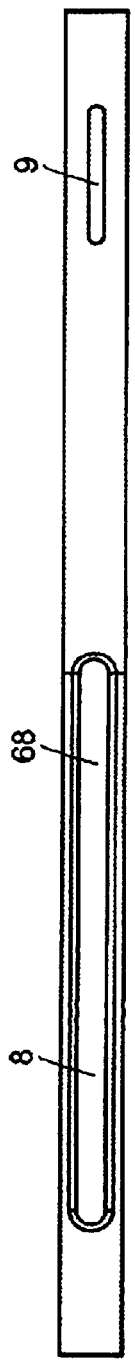
FIG. 3 discloses a side view of a portion of the outside body component of an embodiment of the present invention.

Now referring to FIGS. 1–3, there is provided a device 99 for measuring two points comprising:

a) a hollow tubular body 1 having a proximal portion 3 and a distal portion 5, and a longitudinal bore 61 defining a first opening 7 in the distal portion, b) retraction means 11 having a proximal portion 13 and a distal portion 15, the proximal portion 13 being fixed to the proximal end portion of the hollow tubular body, and the distal portion extending through the first opening of the hollow tubular body, and c) gripping means 21 having a proximal portion 23 and a distal portion 25, the proximal portion of the gripping means being attached to the distal end portion of the retraction means.

The present invention simplifies and coordinates the method of measuring between two points within a surgical site. The device has an body 1 which is preferably substantially cylindrical and hollow with a proximal portion 3 and a tapered distal portion 5. Located on the proximal portion of the hollow outer body is a viewing window 8 (as best seen in FIG. 3). The body 1 also has a plurality of slits 9 (as best seen in FIGS. 1 and 3) located around its distal end portion for ease of sterilization and for facilitating its handling.

Slidably disposed within the hollow outer body 1 is retraction means 11. In these Figures, the retraction means comprises a proximal extension spring 41 and a distal cable 43. The proximal end 12 of the extension spring is fixed by attachment to an outside end cap 14 located on the inner surface of the body 1. The distal end 16 of the extension spring connects to the proximal portion of inner end cap 18 via a loop (not shown) in the distal end of the spring. The proximal portion 19 of cable 43 is also attached to inner cap 18 (which is slidable within the bore), while the distal portion of the cable 43 slidably extends out of first opening 7.

Gripping device 21 is fixedly connected to the distal portion of the cable. In this case, the gripping means comprises a hook 47.

Measuring means 31 comprises numbered ruler 33, viewing window 8, and reference marking 37. Ruler 33 is fixedly attached to the retraction means at a predetermined location (in this case, at inner cap 18) so that its measuring scale 39 is visible through viewing window 35. Ruler 33 has a radially curved shape corresponding to the general curvature of the hollow cylindrical body.

The distal end of the ruler 33 has a tip 40 projecting radially outward from the plane of the ruler and into the slot 68 of the hollow body which defines viewing window 8. The combination of the slot 68 and the tip projecting thereinto provide the device with a stop which prevents significant radial movement of the ruler.

During use of the device in one embodiment, the surgeon advances the distal end of the device through a wound and grips a first connector rod (not shown) with the hook portion of the gripping means. The surgeon then pulls on the body to move the first opening of the body away from the gripping means and towards the second connector rod. During this movement, the spring expands to accommodate the movement and simultaneously pulls ruler 33 along with it. Comparison of the relative change in position of the ruler's measuring scale against the reference marking 37 through the viewing window on the outer body allows calculation of the distance traveled by the opening 7, which corresponds to the distance between the rods. This measured distance provides the size of the cross-connector needed to connect the two rods involved in the measurement.

The body may have any shape which accommodates the retraction means and measuring means. In preferred embodiments, the body component of the device is hollow, is substantially cylindrically-shaped, and has an opening at one end for the slidable extension therethrough of the retraction means. The proximal end of the body may be open or closed. More preferably, the body has a length L and a radius R, wherein the length L is at least ten times the radius R. In these preferred embodiments, the long length of the body allows the surgeon to easily insert the distal portion of the body into a wound while keeping the proximal end thereof outside the body. Thus, these preferred embodiments are particularly useful in endoscopic surgeries requiring access through very small diameter portals.

In some embodiments, the body has longitudinally disposed slits 9 located upon its distal portion which allows the device to be easily sterilized.

In some embodiments, the body further has a measuring slot 68. In some embodiments, the slot functions as a viewing window 8 through which a measuring scale located on the inside of the hollow body and fixedly attached to the retraction device may be seen. In other embodiments, the slot allows for the projection to the outside of the body of a flange which is fixedly attached to the retraction means. In this case, the relative position of the flange may be viewed against a fixed measuring scale disposed on the outside of the body as an alternative way of measuring distance.

In cases where the first and second site are not disposed along the line of site of the tubular body, during use, the retraction means will move laterally within the tubular body until it contacts the rim of the distal end of the tubular body. This lateral movement may cause an unacceptable deviation between the measured and actual distances. Accordingly, in some embodiments, a distal portion of the bore defined by the hollow body is narrowed towards the first opening to from a narrowed distal bore portion 62. This a narrowed distal bore portion 62 restricts the extent of lateral movement of the retraction means possible within the tube, thereby preserving the accuracy of the measurement.

In some embodiments, the distal portion 57 of the outside surface 60 of the body forms a substantially radial concave depression 59. Preferably, this depression extends radially around the entire periphery of the distal end. The shape of this depression can be designed to match the curve of a rod which has been selected as the second measurement site. In use, the concave depression can be easily placed against the curve of the rod to provide stability for ease of measurement.

The retraction means allows both the axial and radial translation of the gripping means relative to the first opening of the body. The axial translation of the gripping means is demonstrated as the ability of the gripping means to move in the longitudinal direction of the tubular body, while the radial translation of the gripping means is demonstrated as the ability of the gripping means to move orthogonally in relation to the longitudinal disposition of the tubular body. The combination of these two capabilities allow the gripping means to reach any point from its initial position (which typically abuts the first opening 7).

The axial and radial translation capability of the gripping means is preferably provided by selecting flexible, longitudinal components for the retraction means. Preferably, at least the distal portion of the retraction mean comprises a flexible, longitudinal component.

In some embodiments, the retraction means comprises a spring. Preferably, the spring is an extension spring. For the purposes of the present invention, an "extension spring" is a coil which is configured so as to provide resistance to movement of its ends in opposite directions. The use of an extension spring in the retraction means provides many advantages when using the device of the present invention. For example, when the device first enters the wound, the minimum resistance provided by the spring is sufficient to keep the gripping means held in place against the first opening of the body (thereby minimizing physical interference by the gripping means). During the measuring step, the surgeon pulls the body away from the gripping means by overcoming the minimum resistance of the spring needed for movement, and so allows the opening of the body to be controllably and precisely moved away from gripping means. Accordingly, in embodiments comprising an extension spring, there is no need to independently control the retraction means when the first opening is moved from its first site within the wound to a second site within the wound. In some embodiments, the retraction means consists essentially of a spring.

In some embodiments, the retraction means comprises a cable. In some embodiments, at least the distal portion of the retraction means comprises a cable. Since the cable may be provided in a relatively small diameter (in relation to the outer diameter formed by a spring), a cable is less likely to interfere with the measuring procedure. In some embodiments, the retraction means consists essentially of a cable, preferably affixed to a spool. Preferably, the spool is located within the body component and is rotated by a flange communicating with the outside of the body.

In some embodiments, the retraction means comprises both a spring and a cable. Preferably, the spring is located at the proximal end of the retraction means while the cable is located at the distal end. This embodiment is advantageous because the retraction means may possess all of the "resistance-related" benefits of the spring embodiment described above, but also provide the "low profile" advantage of a smaller diameter cable at its distal end. In some embodiments thereof, the cable and spring are attached to each other by an end cap.

In an alternate embodiment, the retraction means may comprise a flat portion which is sufficiently thin so as to be curvable around an object to be measured, thereby providing the ability to measure the object's circumference. Preferably, the flat portion is located at the distal end of the retraction means, and is sized so as to be larger than the exit opening of the body. Preferably, the flat portion has a width and a thickness, wherein the width is at least 10 times the thickness. In some embodiments, the surgeon uses a device having this flat portion to measure the circumference of a bone. In these embodiments, the flat portion also has a measuring function.

The gripping means may possess any configuration which allows the surgeon to either a) maintain the location of the gripping means at a first site while moving the first opening to a second site, or b) move the location of the gripping means from a first site to second site while maintaining the location of the first opening. Preferably, the gripping means is selected from the group consisting of a hook, a clip, and a loop.

In some embodiments, the gripping means is a hook configured to attach to the first measuring point within the surgical site. The width of the hook can be made to correspond to the width of an implant to be placed in the body. For example, the hook can be dimensioned so as to match the diameter of rods being implanted. Additionally, the width of the hook can be dimensioned to match the width of a cross connector to be implanted. Advantageously, this embodiment allows for an accurate determination of the size of the cross-connector to be implanted and ensures that the connector will fit on the rod between any screws or hooks which may have already been implanted.

In another embodiment, the gripping device can be a loop. When a loop is used in substantially the same manner as a hook, the surgeon simply loops the loop around a projection in the wound and pulls the first opening of the body away from the projection.

In addition, the loop may also provide particular advantage when used in minimally invasive surgery. In such a surgery (which typically uses a pair of very small access portals in the patient), the device can be inserted through a first portal in the patient and placed adjacent to a first rod or bony landmark. A second device having a hook can then be inserted through the second portal, the hook can be moved towards the loop of the invention, grab the loop, and pull the loop to a second rod or bony landmark. The center-to-center distance between the two rods, the two bony landmarks, or the rod and bony landmark can then be observed on the measuring means of the invention.

In some embodiments, the device further comprises a measuring means. In some embodiments in which the body component of the device comprises a viewing window, the measuring means comprises first ruler located on the inside of the hollow body and affixed to the retraction means with its measuring scale facing outwards. Further, the ruler is affixed in a position which allows its scale to be viewed from the viewing window located on the outside of the body. In this embodiment, the measuring means may further comprise a reference marking located upon the periphery of the viewing window (see for example, reference marking 37, in FIG. 1) which provides the surgeon with a convenient reference for measuring changes in the relative location of the ruler.

In other embodiments in which the body component of the device comprises a distally-located longitudinal slot, the measuring means comprises a first ruler located on the outside of the hollow body with its measuring scale facing outwards. A tab is affixed to the retraction means by means of a projection which is slidably received in the slot. Thus, axial movement of the tab (which is caused by axial movement of the retraction means) is viewed against the fixed scale of the ruler located on the outside of the body. Thus, the measuring means is somewhat similar to that shown in U.S. Pat. No. 4,450,834, the specification of which is incorporated by reference.

In both of the above measuring means embodiments described above, the measuring means comprises one fixed and one movable component (in one case, a movable ruler and a fixed reference marking; in another, a movable tab and a fixed ruler). These components may conveniently be switched to provide the same result.

During use, when the first opening is moved away from the gripping means (or vice versa), the movement causes the retraction means to lengthen and the ruler affixed thereto likewise slides longitudinally within the body along the axis of the retraction means. The relative change in position of the ruler is registered as a distance by comparison of the position of the ruler against the fixed reference marking. The measuring means may use linear components or digital components. The measuring scale can also be visible on a dial rather than through a viewing window in the body.

In other embodiments, the device can have a smaller diameter outer body to allow for easier insertion into surgical site avoiding posterior spinal anatomy. In these embodiments, the outer diameter of the body is no more than 0.5 inches, preferably no more than 0.25 inches.

In some embodiments, the device has particular advantage for use with image-guided surgery systems. In these embodiments, the device is preferably fitted with positioning markers located at the distal end of the body, near the first opening of the outer body. In other embodiments, the device can be used for calibration of electronic measuring devices or used for stereotactic measuring by attaching positioning markers on the proximal end of the body.

In another embodiment, the device further comprises a stop mechanism for preventing the retraction device from retracting before the surgeon can read the measurement in the window once the device reaches the second measuring point. The stop mechanism may include a friction means which engages the retraction device with a level of friction sufficient to overcome the spring retraction force (e.g., in a manner similar to the conventional stop mechanism provided on a tape measure). In some embodiments, the friction means may be manually disengaged to reset the measuring scale. This stop mechanism allows the surgeon to view the measurement accurately and not be concerned with movement from either measuring point while reading the scale on the device.

Alternatively, the measuring scale may comprise a slidable marker slidably disposed around the retraction means. This slidable marker can slide distally from a first position when the retraction means is extended, but stay in place at the distal position when the retraction means retracts. The difference between the first and distal position corresponds to the distance between the two surgical sites.

The device may be made of materials typically selected for use in surgical instruments. In some embodiments, the spring, cable, tip and clips are made of stainless steel, while the hook, tube and ends are made of aluminum. Preferably, at least the gripping means component of the device is sterile. More preferably, the entire device is sterile.

One embodiment of the device is available from DePuy AcroMed, Inc. of Raynham, Mass. as the Crossover Guide.

The present invention relates to a surgical device for determining the distance between two points within a surgical site. Additionally, the device can be used to determine the corresponding size of an implant to be placed in a surgical site between two points. For example, in a spinal surgery where adjacent vertebrae are stabilized by two parallel rods fixed to the vertebrae by screws, this device can be used to determine the size of a cross-connector needed to connect the two parallel rods and thereby enhance the stability of the construct. In accordance with the present invention, a device is provided that is capable of accurately measuring the distance between two points in a surgical wound while displaying the measurement outside the wound.

In embodiments in which the surgeon measures the distance between connector rods, the gripping means preferably allows the surgeon to grip one rod, pull the body of the device to the other rod and read the measurement on the measuring scale along the outer body of the device outside the wound. The measurement would correspond to the size of the cross-connector that would fit across the two rods.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. A method of determining distance between two sites in a surgical wound, comprising;
   a) providing a measuring device comprising a device for measuring two points comprising:
      i) a hollow tubular body having a proximal portion and a distal portion, and a longitudinal bore defining a first opening in the distal portion,
      ii) retraction means having a proximal spring portion and a distal portion comprising a cable, the proximal spring portion being longitudinally disposed within the longitudinal bore and fixed to the proximal end portion of the hollow tubular body, and the distal portion extending through the first opening of the hollow tubular body, and iii) gripping means having a proximal portion and a distal portion, comprising a hook portion, the proximal portion of the gripping means being attached to the distal end portion of the retraction means, b) locating the device at a first site within the surgical wound, c) moving either the first opening or the gripping means to a second site within the surgical wound while maintaining either the first opening or the gripping means at the first site, and d) viewing a measuring scale.

2. The method of claim 1 wherein the gripping means is moved to a second site while the first opening is maintained at the first site.

3. The method of claim 1 wherein the first opening is moved to a second site while the gripping means is maintained at the first site.

4. The method of claim 1 wherein the gripping means grips a first connector rod with the hook portion of the gripping means.

* * * * *